(12) United States Patent
Bierleutgeb

(10) Patent No.: US 7,632,469 B2
(45) Date of Patent: Dec. 15, 2009

(54) SPECIMEN HOLDER FOR SPECIMENS FOR HIGH-PRESSURE FREEZING AND HIGH-PRESSURE FREEZING DEVICE HAVING A SPECIMEN HOLDER

(75) Inventor: Fritz Bierleutgeb, Kilb (AT)

(73) Assignee: Leica Mikrosysteme GmbH, Vienna (AT)

( * ) Notice: Subject to any disclaimer, the term of this patent is extended or adjusted under 35 U.S.C. 154(b) by 777 days.

(21) Appl. No.: 11/382,543

(22) Filed: May 10, 2006

(65) Prior Publication Data

US 2006/0255520 A1 Nov. 16, 2006

(30) Foreign Application Priority Data

May 12, 2005 (DE) .................. 10 2005 021 962

(51) Int. Cl.
*B01L 3/00* (2006.01)
(52) U.S. Cl. .................. 422/102; 62/62; 62/543; 100/38; 100/211; 220/592.01
(58) Field of Classification Search .............. 422/102; 62/62, 543, 115; 100/38, 211; 220/592.01
See application file for complete search history.

(56) References Cited

U.S. PATENT DOCUMENTS

| 2,662,520 | A | 12/1953 | McMahon |
| 4,688,387 | A | 8/1987 | Conaway |
| 6,516,620 | B2 | 2/2003 | Lang |
| 2002/0059802 | A1* | 5/2002 | Lang .......................... 62/62 |
| 2002/0079318 | A1 | 6/2002 | Wurzinger |

FOREIGN PATENT DOCUMENTS

JP 2004198347 A 7/2004

OTHER PUBLICATIONS

Leica Mikrosysteme GmbH, "Leica EM PACT, High Pressure Freezer according to Studer", Vienna, Austria, Dec. 2003, Order No. 165002, pp. 1-11 and inserts.

* cited by examiner

*Primary Examiner*—Michael A Marcheschi
*Assistant Examiner*—Jonathan M Hurst
(74) *Attorney, Agent, or Firm*—Hodgson Russ LLP

(57) ABSTRACT

A specimen holder for a high-pressure freezing device comprises a first shaped part (2) and a second shaped part (3) that form, in the mutually joined state, a specimen space (6). The first shaped part (2) is embodied in a cup shape, and possesses a bottom (5) that closes off the specimen chamber (6) toward the outside to prevent contact between the specimen and a pressure medium.

12 Claims, 3 Drawing Sheets

SPECIMEN HOLDER FOR SPECIMENS FOR HIGH-PRESSURE FREEZING AND HIGH-PRESSURE FREEZING DEVICE HAVING A SPECIMEN HOLDER

CROSS REFERENCE TO RELATED APPLICATIONS

This application claims priority of the German patent application 10 2005 021 962.4-52 filed May 12, 2005 which is incorporated by reference herein.

FIELD OF THE INVENTION

The invention relates to a specimen holder for specimens for high-pressure freezing. The invention relates in particular to a specimen holder for specimens for high-pressure freezing in which the specimen holder comprises at least one first and one second shaped part. The first shaped part and second shaped part form, in the mutually joined state, a specimen space 6 in which the specimen to be frozen is deposited.

The invention further relates to a high-pressure freezing device having a specimen holder. The invention relates in particular to a high-pressure freezing device having a clamping apparatus for a specimen holder. The specimen holder comprises at least one first and one second shaped part; the clamping apparatus is made up of a first part and a second part that join the first shaped part and the second shaped part to one another and thus enclose the specimen in a specimen space.

BACKGROUND OF THE INVENTION

German Patent Application DE 100 15 773 A1 discloses a specimen holder for aqueous specimens for freezing under high pressure in a high-pressure freezing device. The specimen holder possesses a housing sheath in which a cutout is defined. A specimen retention element is arranged in the cutout of the specimen holder and can be sprayed from both sides, through the cutout, with a coolant. The specimen retention element is constructed from at least one first part and one second part, a recess for specimen reception being shaped into the second part. The second part is pressed with a screw against the first part so that the recess is closed off in pressure-tight fashion. Acting as counter-element for the screw is a further element which comprises a pressure inlet that terminates directly in the sample receptacle. Upon application of high pressure to the specimen holder, the pressure medium that is used thus comes into contact with the specimen.

German Patent Application DE 100 65 143 A1 discloses a specimen holder for a high-pressure freezing device. The specimen holder is made up of at least two shaped parts, detachably joinable to one another, that in the joined state form a receptacle for a specimen. At least one of the shaped parts comprises, on the side facing toward the receptacle, a diamond coating or diamonds themselves. Associated with the shaped part having the specimen receptacle is a further shaped part having a high-pressure conduit. The high-pressure conduits communicates with an orifice that terminates in the specimen chamber. In this fashion, the pressure medium acts directly on the specimen present in the specimen receptacle in order to generate the pressure necessary for high-pressure freezing.

The high-pressure freezing machine of the Balzers company, having the model designation HPM 010, likewise discloses a two-part sample holder in which a separate chamber is constituted. In this apparatus as well, the pressure medium acts directly on the specimen located in the specimen chamber.

The high-pressure freezing device having the model designation "Leica EM HPF" likewise discloses a two-part specimen holder that constitutes a specimen space into which the specimen to be frozen can be introduced. Liquid nitrogen at a pressure of approximately 2100 bar is forced into the freezing chamber by the high-pressure freezing device. The specimen itself is protected by two small aluminum plates, and floats for approximately 40 ms in an alcohol before the liquid nitrogen is introduced under high pressure into the specimen chamber.

The brochure for the "LEICA EM PACT" describes a high-pressure freezing device, having several variants, for retaining specimens for high-pressure freezing. The specimens are placed into a part of the specimen holder that comprises an orifice that is in communication with the pressure medium being used. The pressure medium thus acts directly on the specimen. In addition, these parts of the specimen holders are difficult to produce using mechanical machining processes.

SUMMARY OF THE INVENTION

It is therefore the object of the present invention to create a specimen holder for specimens for high-pressure freezing that avoids direct contact between the specimen and the pressure medium, and is easy to produce.

A further object of the invention is to create a high-pressure freezing device in which direct contact between the pressure medium and the specimen to be frozen is avoided.

It is advantageous if the specimen holder for specimens for high-pressure freezing is made up of at least one first and one second shaped part; and that the first shaped part and the second shaped part form, in the mutually joined state, a specimen space. The first shaped part is embodied in a cup shape, and a bottom of the first shaped part closes off the specimen space to the outside.

The bottom of the first shaped part rests on a holder that is embodied with an orifice that terminates at the bottom of the first shaped part. Through the orifice, a pressure generated by a pressure medium is applied to the bottom of the first shaped part. The bottom of the first shaped part is dimensioned in such a way that a pressure is applied to the specimen without any contact between the specimen and the pressure medium.

The bottom is embodied as a membrane that is retained in an annular holder. The bottom of the first shaped part has a thickness that is in the range between 100 µm and 20 µm. The first shaped part is produced by etching from an annular copper sheet.

At least one surface of the second shaped part, which surface is located opposite the specimen in the first shaped part, is equipped with a diamond. The entire second shaped part can also be made of a diamond.

The high-pressure freezing device encompasses a clamping apparatus for a specimen holder. The specimen holder comprises at least one first and one second shaped part, the clamping apparatus being made up of a first part and a second part. The first shaped part and the second shaped part are Joined to one another by the clamping apparatus, a specimen being enclosed in a specimen space. The first shaped part is embodied in a cup shape, and a bottom of the first shaped part closes off the specimen space to the outside. The first part of the clamping apparatus encompasses a pressure inlet passage that coacts with the bottom of the first shaped part by communication therewith.

The clamping apparatus closes off the first shaped part and the second shaped part, and thus also the specimen space, in pressure-tight fashion.

The second part of the clamping apparatus is a screw that coacts with the second shaped part and thus presses the second shaped part against the first shaped part. The first part of the clamping apparatus is a counter-element to the second part of the clamping apparatus.

The use of a first shaped part of a specimen holder in a high-pressure freezing device is advantageous if the first shaped part of the specimen holder is produced by etching from a disk-shaped starting material. The starting material is copper. The first shaped part is embodied in a cup shape as a result of the etching, and thus possesses a bottom that possesses a thickness of 20 μm to 100 μm.

Further advantageous embodiments of the invention may be inferred from the dependent claims, and are the subject matter of the Figures below and the descriptions thereof.

DETAILED DESCRIPTION OF THE INVENTION

Figure 1:
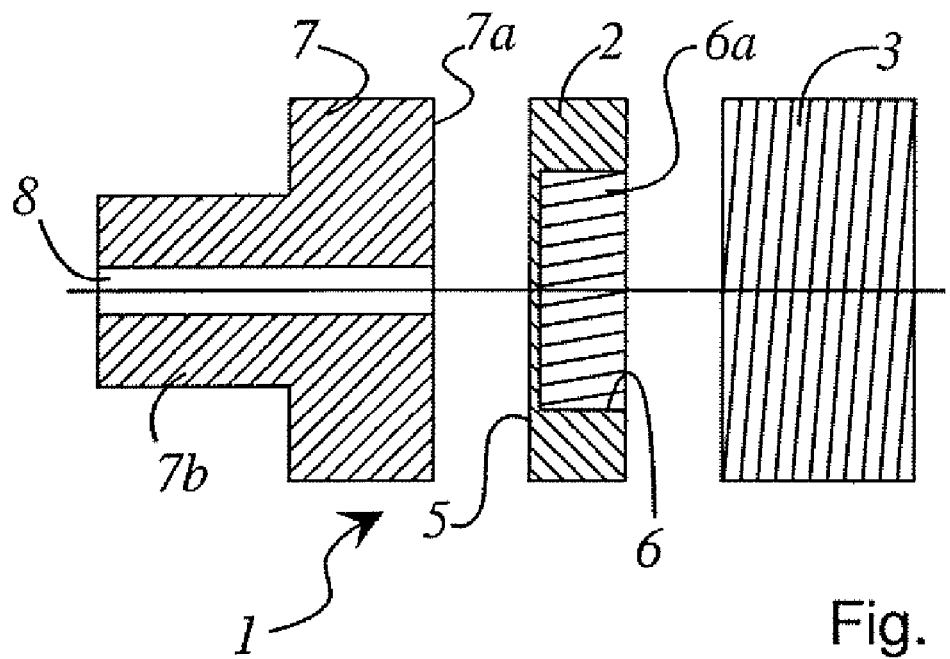
FIG. 1 is a cross section showing the arrangement of the various parts of a specimen holder in accordance with the present invention.

FIG. 1 is a cross section through a specimen holder 1 for specimens for high-pressure freezing. The specimen holder is made up of at least one first shaped part 2 and one second shaped part 3 which, in the mutually joined state, form a specimen space 6 into which a specimen 6a to be frozen can be introduced. First shaped part 2 is embodied in a cup shape and is equipped with a bottom 5 that closes off first shaped part 2 to the outside. Bottom 5 of first shaped part 2 rests on a holder 7. Holder 7 is embodied with an orifice that terminates at bottom 5 of the first shaped part. Through orifice 8 in holder 7, the pressure medium can act on bottom 5 of the first shaped part. Because of the cup-shaped configuration of first shaped part 2, specimen space 6 is thus completely closed off when second shaped part 3 is also in contact against first shaped part 2. The result of this arrangement is that external fluids cannot come into contact with specimen 6a.

Figure 2:
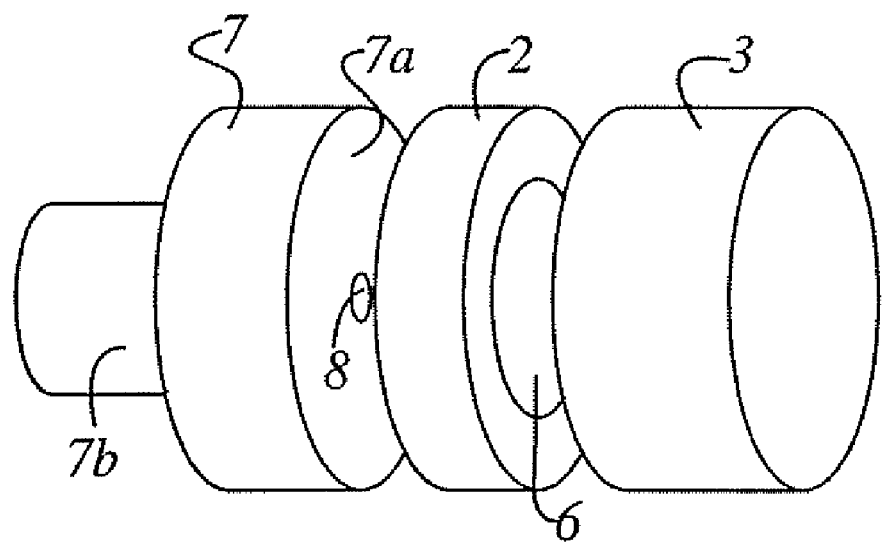
FIG. 2 is an exploded perspective depiction of a specimen holder in accordance with the present invention.

FIG. 2 is an exploded perspective depiction of specimen holder 1 in accordance with the present invention. First shaped part 2 is introduced between holder 7 and second shaped part 3. First shaped part 2 is embodied in a cup shape, and thereby generates a specimen space 6 into which specimen 6a that is to be examined can be introduced. First shaped part 2 and second shaped part 3 are configured with a circular cross section, and possess an identical diameter. Holder 7 comprises an end 7a, facing toward first shaped part 2, that is likewise circular in shape and has the same diameter as first shaped part 2. Holder 7 furthermore comprises an extension 7b that possesses a smaller diameter than front end 7a of holder 7. Guided in extension 7b is orifice 8 that ultimately terminates at bottom 5 of first shaped part 2.

Figure 3:
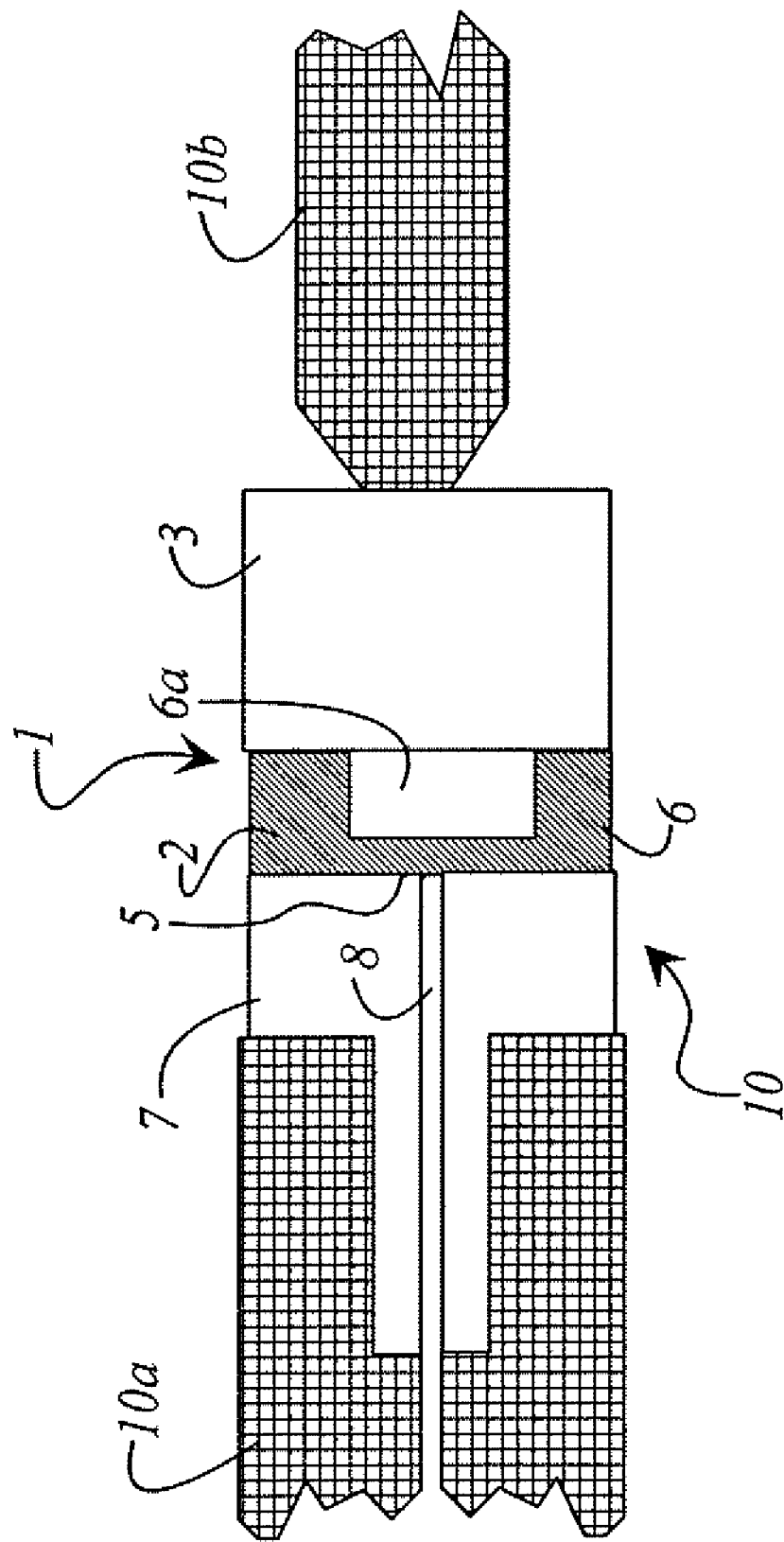
FIG. 3 schematically shows the arrangement of the specimen holder in a high-pressure freezing device.

FIG. 3 schematically shows a high-pressure freezing device having a clamping device 10 for specimen holder 1. Specimen holder 1 is made up of first shaped part 2 and second shaped part 3, which are joined to one another by clamping apparatus 10. The clamping apparatus is made up of a first part 10a and a second part 10b which, in coaction, join first shaped part 2 and second shaped part 3 to one another in such a way that specimen 6a is enclosed in specimen space 6. Bottom 5 of first shaped part 2 rests on a holder 7. Holder 7 coacts with first part 10a of clamping apparatus 10. Second shaped part 3 coacts with second part 10b of clamping apparatus 10. Bottom 5 of first shaped part 2 is dimensioned in such a way that a pressure is applied to specimen 6a without contact between specimen 6a and the pressure medium. Bottom 5 is embodied as a membrane, and possesses a thickness in a range between 20 μm and 100 μm. Second part 10b of clamping apparatus 10 is a screw that coacts with second shaped part 3. Screwing in the screw causes second shaped part 3 to be pressed against first shaped part 2 and likewise against holder 7. First shaped part 10a of clamping apparatus 10 forms a countermember, and thus also creates the pressure inlet to holder 7 through a pressure inlet passage 12 aligning with orifice 8 of holder 7.

Figure 4:
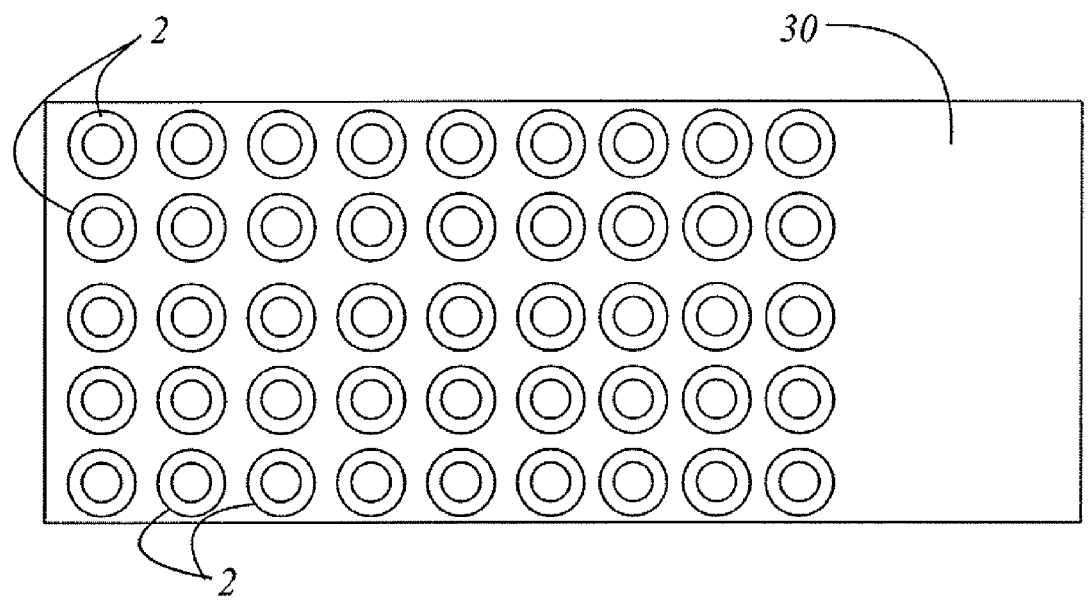
FIG. 4 shows an arrangement of multiple shaped parts of the specimen holder that were produced using an etching process.

FIG. 4 shows an arrangement of multiple first shaped parts 2 that are produced on a support 30 by means of an etching process. The etching process makes it possible to produce, from thin sheet-copper disks, a first shaped part 2 having a very thin bottom 5. The thickness of the bottom can typically be between 30 μm and 50 μm. Bottom 5 can therefore also be referred to as a membrane. The sheet-copper disks are applied onto support 30 in a regular arrangement, and the cup-shaped structure of first shaped part 2 is then produced by way of the etching process.

Figure 5:
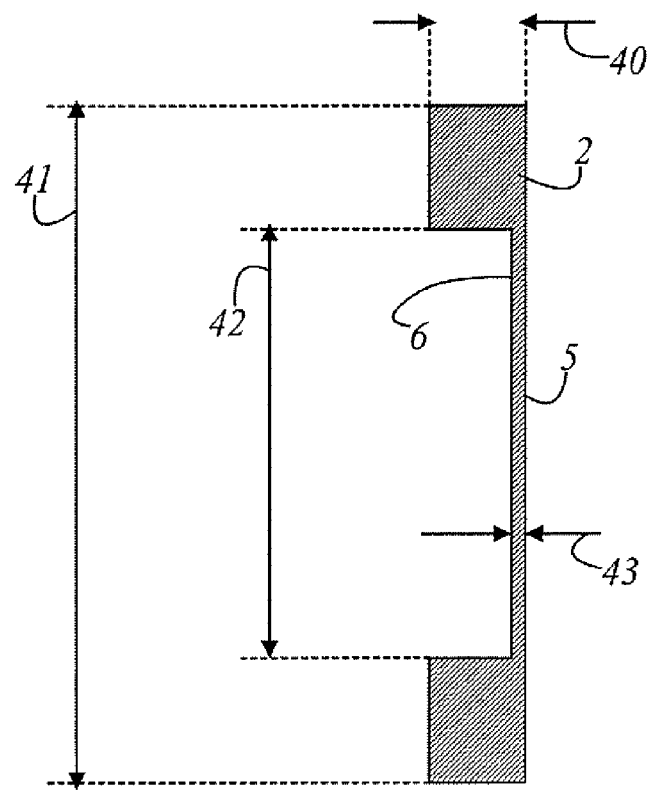
FIG. 5 is a cross-section through the part of the specimen holder that is cup-shaped in order to receive the specimen.

FIG. 5 is a cross section of first shaped part 2 of specimen holder 1. As already mentioned in the description of FIG. 4, first shaped part 2 of specimen holder 1 is produced from a sheet-copper disk by means of an etching process. The sheet-copper disk has a thickness 40 of approximately 0.25 mm. Diameter 41 of the sheet-copper disk is approximately 2.8 mm. The etching process generates a specimen space 6 having a diameter 42 of approximately 1.5 mm. By way of the etching process, material having a thickness of approximately 0.2 mm is removed from the sheet-copper disk. The result is a bottom 5 of first shaped part 2 that has a thickness 43 of approximately 50 μm to 20 μm.

What is claimed is:

1. An apparatus for holding a specimen during freezing of the specimen while the specimen is in a high-pressure state caused by a pressure medium, the apparatus comprising: a first shaped part in the shape of a cup, the first shaped part having a bottom comprising a membrane and an open top opposite the bottom; a second shaped part for engaging the open top of the first shaped part in a mutually joined state to define a specimen space, wherein the specimen space is completely closed to the outside such that the pressure medium cannot directly contact the specimen the apparatus further comprising a holder having an orifice therethrough, wherein the bottom of the first shaped part engages the holder such that the orifice terminates at the bottom of the first shaped part, wherein a pressure generated by the pressure medium is applied through the orifice to the bottom of the first shaped part, and wherein the bottom is dimensioned such that a pressure is applied to the specimen without any direct contact between the specimen and the pressure medium.

2. The apparatus according to claim 1, wherein the first shaped part includes an annular holder retaining the membrane.

3. The apparatus according to claim 1, wherein the bottom of the first shaped part has a thickness in a range from 100 μm through 20 μm.

4. The apparatus according to claim 3, wherein the first shaped part is produced by etching.

5. The apparatus according to claim 1, wherein the second shaped part includes a surface that engages the first shaped part to cover the open top of the first shaped part, and the surface of the second shaped part includes diamond.

6. The apparatus according to claim 5, wherein the second shaped part is made of diamond.

7. A device for holding a specimen during high-pressure freezing, the device comprising: a clamping apparatus including a first part and a second part opposite the first part, the first part having a pressure inlet passage therethough; a specimen holder including a first shaped part and a second shaped part joined together by the clamping apparatus to define a specimen space for holding a specimen, wherein the specimen space is completely closed to the outside; wherein the first shaped part of the specimen holder has a bottom comprising a membrane and an open top opposite the bottom, and the second shaped part covers the open top of the first shaped part when the first shaped part and the second shaped part are joined together by the clamping apparatus; and wherein the pressure inlet passage of the first part of the clamping apparatus is in communication with the bottom of the first shaped part of the specimen holder wherein the clamping apparatus joins the first shaped part and the second shaped part in pressure-tight fashion during high-pressure freezing; the device further comprising a holder between the first part of the clamping apparatus and the first shaped part of the specimen holder, wherein the holder includes an orifice therethrough terminating at the bottom of the first shared part for providing communication between the pressure inlet passage of the first part of the clamping apparatus and the bottom of the first shaped part of the specimen holder wherein a pressure generated by a pressure medium is applied through the orifice to the bottom of the first shaped part and wherein the bottom of the first shaped part is dimensioned such that a pressure is applied to the specimen without any direct contact between the specimen and the pressure medium.

8. The device according to claim 7, wherein the first shaped part includes an annular hold retaining the membrane.

9. The device according to claim 7, wherein the bottom of the first shaped part has a thickness in a range from 100 μm through 20 μm.

10. The device according to claim 7, wherein the second shaped part includes a surface that engages the first shaped part to cover the open top of the first shaped part, and the surface of the second shaped part includes diamond.

11. The device according to claim 7, wherein the second part of the clamping apparatus is a screw that presses against the second shaped part of the specimen holder to press the second shaped part of the specimen holder against the first shaped part of the specimen holder.

12. The device according to claim 9, wherein the first shaped part is produced by etching.

* * * * *